United States Patent [19]

Roe et al.

[11] Patent Number: 5,391,369
[45] Date of Patent: Feb. 21, 1995

[54] GELLED POLYVINYL ALCOHOL BIOCIDAL TREATMENTS

[75] Inventors: Donald C. Roe, Tabernacle, N.J.; David M. Polizzotti, Yardley, Pa.

[73] Assignee: Betz Laboratories, Inc., Trevose, Pa.

[21] Appl. No.: 105,088

[22] Filed: Aug. 10, 1993

Related U.S. Application Data

[62] Division of Ser. No. 47,729, Apr. 15, 1993, Pat. No. 5,266,218.

[51] Int. Cl.$^6$ ............... A61K 31/74; A01N 25/10
[52] U.S. Cl. ...................... 424/78.37; 424/78.08
[58] Field of Search .................................. 424/78.37

[56] References Cited

U.S. PATENT DOCUMENTS

| | | | |
|---|---|---|---|
| 3,426,134 | 2/1969 | Shema et al. | 424/302 |
| 3,908,680 | 9/1975 | Krezanoski | 134/27 |
| 4,251,643 | 2/1981 | Harada et al. | 525/61 |
| 4,331,781 | 5/1982 | Zimmermann et al. | 525/61 |
| 4,559,186 | 12/1987 | Lee | 525/61 |
| 4,722,801 | 2/1988 | Bunczk et al. | 252/106 |
| 4,780,236 | 10/1988 | Bunczk et al. | 252/174 |
| 4,863,972 | 9/1989 | Itagaki et al. | 525/61 |
| 5,258,136 | 11/1993 | Smith et al. | 252/315.4 |

*Primary Examiner*—Thurman K. Page
*Assistant Examiner*—Peter F. Kulkosky
*Attorney, Agent, or Firm*—Alexander D. Ricci; Richard A. Paikoff

[57] ABSTRACT

A biocidal composition and method for inhibiting and controlling the growth of microorganisms are disclosed. The composition comprises an amount, effective for the intended purpose, of polyvinyl alcohols and gallic or boric acids, in combination with additional biocidal components, the composition in a gel form. The method comprises administering an amount of the gelled composition to the particular water containing system for which treatment is desired.

3 Claims, No Drawings

GELLED POLYVINYL ALCOHOL BIOCIDAL TREATMENTS

This is a divisional of application Ser. No. 08/047,729, filed Apr. 15, 1993, now U.S. Pat. No. 5,266,218.

BACKGROUND OF THE INVENTION

The formation of slimes by microorganisms is a problem that is encountered in many aqueous systems. For example, the problem is not only found in natural waters such as lagoons, lakes, ponds, etc., and confined waters as in pools, but also in such industrial systems as cooling water systems, air washer systems and pulp and paper mill systems. All possess conditions which are conducive to the growth and reproduction of slime-forming microorganisms. In both once-through and recirculating cooling systems, for example, which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms flourish on the tower proper, while other organisms colonize and grow in such areas as the tower sump and the piping and passages of the cooling system. The slime formation not only aids in the deterioration of the tower structure in the case of wooden towers, but also, by its deposition on metal surfaces, promotes corrosion. In addition, slime carried through the cooling system plugs and fouls lines, valves, strainers, etc., and deposits on heat exchange surfaces. In the latter case, the impedance of heat transfer can greatly reduce the efficiency of the cooling system.

In pulp and paper mill systems, slime formed by microorganisms is commonly encountered and causes fouling, plugging, or corrosion thereof. The slime also becomes entrained in the paper produced to cause breakouts on the paper machines, with consequent work stoppages and the loss of production time, and/or is responsible for unsightly blemishes in the final product, which result in rejects and wasted output.

The previously discussed problems have resulted in the extensive utilization of biocides in cooling water and pulp and paper mill systems. Materials which have enjoyed widespread use in such applications include chlorine, chlorinated phenols, organo-bromines, and various organo-sulfur compounds. All of these compounds are generally useful for this purpose but each is attended by a variety of impediments. For example, chlorination is limited both by its specific toxicity for slime-forming organisms at economic levels and by the tendency of chlorine to react, which results in the expenditure of the chlorine before its full biocidal function is achieved. Other biocides are attended by odor problems and hazards in respect to storage, use or handling which limit their utility. To date, no one compound or type of compound has achieved a clearly established predominance in respect to the applications discussed. Likewise, lagoons, ponds, lakes, and even pools, either used for pleasure purposes or for industrial purposes for the disposal and storage of industrial wastes, become, during the warm weather, besieged by slime due to microorganism growth and reproduction. In the case of recreational areas, the problem of infection is obvious. In the case of industrial storage or disposal of industrial materials, the microorganisms cause additional problems which must be eliminated prior to the materials' use or disposal of the waste.

Naturally, economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides has exhibited a prolonged biocidal effect. Instead, their effectiveness is rapidly reduced as a result of exposure to physical conditions such as temperature, association with ingredients contained by the system toward which they exhibit an affinity or substantivity, etc., with a resultant restriction or elimination of their biocidal effectiveness, or by dilution.

In addition, the majority of the previously discussed biocides are liquid, organic solvent-based formulations, which may pose environmental, health and safety concerns. With increasing public awareness and governmental legislation related to chemical spills, environmental hazards, and health and safety in the workplace, improved methods of formulating, packaging and handling biocides are of growing interest.

SUMMARY OF THE INVENTION

The biocidal compositions of the present invention comprise gelled, water and/or polymer based mixtures of 1) an isothiazolin compound or 2) a quaternary ammonium salt and 2-bromo-2-nitropropane-1,3-diol, with 1) or 2) combined with polyvinyl alcohols and gallic or boric acid crosslinking agents.

DETAILED DESCRIPTION OF THE PREFERRED EMBODIMENTS

The present invention provides an improvement over previous biocide formulations and applications techniques. It has been discovered that biocides may be formulated as water and/or polymer-based products which are gels at ambient (less than 120° F.) temperatures. The gelled biocides are essentially in a plastic, semi-solid or waxy form, and can be supplied as a bulk gel in buckets or drums, in molded form (gel logs or briquettes), or as a bulk solid (gel beads or flakes). The advantages of gelled biocides are reduced spill hazards, reduced odor, fire and explosion hazards, and improved handling and worker safety. The elimination of organic solvents provides both an economic and health and safety advantage.

The following examples illustrate the feasibility of gelled biocide technology. In addition, many other formulations and applications are possible which would be obvious to those skilled in the art, and all such modifications should be considered within the scope and spirit of this invention.

I. Isothiazolin

This formulation contains the following components:

|  | Approximate Weight Percentages |
|---|---|
| Water | 78% |
| Polyvinyl alcohol | 10% |
| 5-Chloro-2-methyl-4-isothiazolin-3-one | 11% |

| | Approximate Weight Percentages |
|---|---|
| Gallic acid | 1% |

CMIT: 5-chloro-2-methyl-4-isothiazolin-3-one

The means of preparation of this formulation is as follows: Water is added to a heated vessel with an overhead stirrer. The polyvinyl alcohol is slowly added to cold water with constant stirring and mixed until dispersed (approximately 10 minutes). The polyvinyl alcohol dispersion is then heated to 180° F. with constant stirring until dissolved (approximately 1 hour at 180° F.). The solution is then cooled to 150° F., and the 5-chloro-2-methyl-4-isothiazolin-3-one compound, gallic acid and a trace of cupric nitrate are added and stirred to mix. The solution is slowly cooled until thick, (at approximately 120° F.) poured into containers or molds, and allowed to gel.

This gelled biocide is thermally reversible, with a melting point of approximately 100°-200° F. A drum containing the gel may be heated prior to application and applied using a normal metering pump through heat traced tubing. It is believed that the gel will be soluble in cold water, whereby the biocide could be delivered on a time-release basis, with the rate of release dependent on a process slip-stream flow rate and temperature. A borate/boric acid crosslinking agent in lieu of the gallic acid may also be used, whereby the biocide release mechanism could be based on a pH trigger. Alternatively, the formulation could be prepared with boric acid, in an acidic pH, and sprayed into an alkaline solution, forming a crosslinked PVOH/borate shell for biocide bead formation.

The following weight ranges of particular components are anticipated to be effective: 50-90% water, 1-20% polyvinyl alcohol, 5-20% isothiazolin (e.g., CMIT) and 0.1-2% gallic acid.

II. Quaternary Ammonium Halide Salt/BNPD

This formulation contains the following components:

| | Approximate Weight Percentages |
|---|---|
| Water | 74% |
| Polyvinyl alcohol | 10% |
| Quaternary alkyldimethylbenzyl ammonium chloride (quat) | 10% |
| 2-bromo-2-nitropropane-1,3-diol (BNPD) | 5% |
| Gallic Acid | 1% |

The means of preparation is the same as that for the Isothiazolin example described above through the first cooling stage. The quaternary alkyldimethylbenzyl ammonium chloride and 2-bromo-2-nitropropane-1,3-diol compounds are added and stirred until mixed, followed by the addition and mixing of gallic acid. The solution is cooled with constant stirring until it thickens, and is poured into molds or containers. It requires approximately 24 to 48 hours to gel after cooling. The gel is thermally reversible once it is formed, with a melting point of from about 100°-200° F.

The following weight ranges of particular components are anticipated to be effective: 50-90% water, 1-20% polyvinyl alcohol, 5-20% quaternary ammonium halide salt (e.g., quat), 2.5-10% BNPD and 0.1-2.0% gallic acid.

In accordance with the present invention, the gelled biocidal treatments, described above may be added to the desired aqueous system in need of biocidal treatment, in an amount of from about 0.1 to about 200 parts of the treatment to one million parts (by weight) of the aqueous medium. Preferably, about 5 to about 50 parts of the treatment per one million parts (by weight) of the aqueous medium is added.

While we have shown and described herein certain embodiments of the present invention, it is intended that there be covered as well any change or modification therein which may be made without departing from the spirit and scope of the invention.

We claim:

1. A gelled biocidal composition comprising about 1-20 weight percent of a polyvinyl alcohol and about 0.1-2 weight percent of gallic or boric acid, in combination with additional components selected from the group consisting of:
   (a) about 5-20 weight percent of an isothiazolin compound or, alternatively,
   (b) about 5-20 weight percent of a quaternary ammonium halide salt and about 2.5-10 weight percent of 2-bromo-2-nitropropane-1,3-diol with the remainder of the composition being water.

2. The composition as recited in claim 1 wherein said isothiazolin compound is 5-chloro-2-methyl-4-isothiazolin-3-one.

3. The composition as recited in claim 1 wherein said quaternary ammonium halide salt is a quaternary alkyldimethylbenzyl ammonium chloride.

* * * * *